US009278957B2

(12) United States Patent
Kogan et al.

(10) Patent No.: US 9,278,957 B2
(45) Date of Patent: Mar. 8, 2016

(54) PIPERAZINE, PIPERIDINE AND TETRAHYDROPYRIDINE DERIVATIVES AND THEIR PHARMACEUTICAL USE

(71) Applicant: ATIR Holding S.A., Luxembourg (LU)

(72) Inventors: Vladimir Kogan, Rechovot (IL); Lev Tabachnik, Kiryat-Ono (IL)

(73) Assignee: ATIR Holding S.A., Luxembourg (LU)

( * ) Notice: Subject to any disclaimer, the term of this patent is extended or adjusted under 35 U.S.C. 154(b) by 0 days.

(21) Appl. No.: 14/569,828

(22) Filed: Dec. 15, 2014

(65) Prior Publication Data

US 2015/0099784 A1   Apr. 9, 2015

Related U.S. Application Data

(62) Division of application No. 13/322,572, filed as application No. PCT/IL2010/000418 on May 26, 2010, now Pat. No. 8,912,196.

(60) Provisional application No. 61/181,331, filed on May 27, 2009.

(51) Int. Cl.
*C07D 405/06* (2006.01)
*C07D 307/91* (2006.01)
*C07D 407/06* (2006.01)
*C07D 407/12* (2006.01)
*C07D 407/14* (2006.01)

(52) U.S. Cl.
CPC ............ *C07D 405/06* (2013.01); *C07D 307/91* (2013.01); *C07D 407/06* (2013.01); *C07D 407/12* (2013.01); *C07D 407/14* (2013.01)

(58) Field of Classification Search
CPC .. C07D 307/91; C07D 407/06; C07D 407/12; C07D 407/14; C07D 405/06
USPC .......................................... 514/320; 546/214
See application file for complete search history.

(56) References Cited

U.S. PATENT DOCUMENTS 3,701,786 A * 10/1972 Hopps et al. ......... C07D 295/02
                                                 250/396 R
3,751,390 A *  8/1973 Hopps et al. ......... C07D 307/91
                                                 250/396 R
3,959,309 A    5/1976 Mooradian
2012/0071487 A1 3/2012 Kogan et al.
2013/0023541 A1 1/2013 Boehm et al.

FOREIGN PATENT DOCUMENTS

DE           19648384         5/1998
WO    WO 2010/137018         12/2010

OTHER PUBLICATIONS

Communication Pursuant to Article 94(3) EPC Dated Oct. 8, 2013 From the European Patent Office Re. Application No. 10725881.6.
Examiner-initiated interview Summary Dated Jul. 9, 2014 From the US Patent and Trademark Office Re. U.S. Appl. No. 13/322,572.
International Preliminary Report on Patentability Dated Aug. 26, 2011 From the International Preliminary Examining Authority Re. Application No. PCT/IL2010/000418.
International Search Report and the Written Opinion Dated Sep. 22, 2010 From the International Searching Authority Re. Application No. PCT/IL2010/000418.
Official Action Dated Aug. 19, 2013 From the US Patent and Trademark Office Re. U.S. Appl. No. 13/322,572.
Official Action Dated Feb. 28, 2014 From the US Patent and Trademark Office Re. U.S. Appl. No. 13/322,572.
Restriction Official Action Dated May 17, 2013 From the US Patent and Trademark Office Re. U.S. Appl. No. 13/322,572.
Arlt et al. "Preparation of Fluorenes, Dibenzofurans and Dibenzothiophenes as Dopamine D4 Receptor Ligands", Database GenBank CAPLUS [Online], AN: 1998:351832, DN: CA129:41150, 6 P., 1998.
Arlt et al. "SAR of Novel Biarylmethylamine Dopamine D4 Receptor Ligands", Bioorganic & Medicinal Chemistry Letters, XP004137181, 8(15): 2033-2038, Aug. 4, 1998. p. 2036-2037, Table 3, Compound 8b.
Lander et al. "The Dipole Moments of Catechol, Resorcinol and Hydroquinone", Journal of the American Chemical Society, JACS, 67: 322-324, Feb. 1945.
Metalife "2-[4-(Dibenzofuran-4-Ylmethyl)Piperazin-1-Yl]Pyrimidine", Metalife AG, Drug2Gene, Entry ID: 206692517, Version 2.3, 5 P., Jan. 10, 2014.
Wikipedia "Agonist", From Wikipedia, the Free Encyclopedia, 4 P., Last Modified Aug. 3, 2014.
Wikipedia "IC50", From Wikipedia, the Free Encyclopedia, 4 P., Last Modified May 31, 2014.
Wikipedia "Phenol", Wikipedia, the Free Encyclopedia, p. 1-4, 2013.
Wikipedia "Receptor Antagonist", Wikipedia, the Free Encyclopedia, p. 1-6, 2014.

* cited by examiner

*Primary Examiner* — Celia Chang

(57) ABSTRACT

Novel piperazine, piperidine and tetrahydropyridine derivatives comprising a dibenzofurane moiety are provided herein, as well as pharmaceutical compositions comprising same and therapeutic uses thereof.

15 Claims, 1 Drawing Sheet

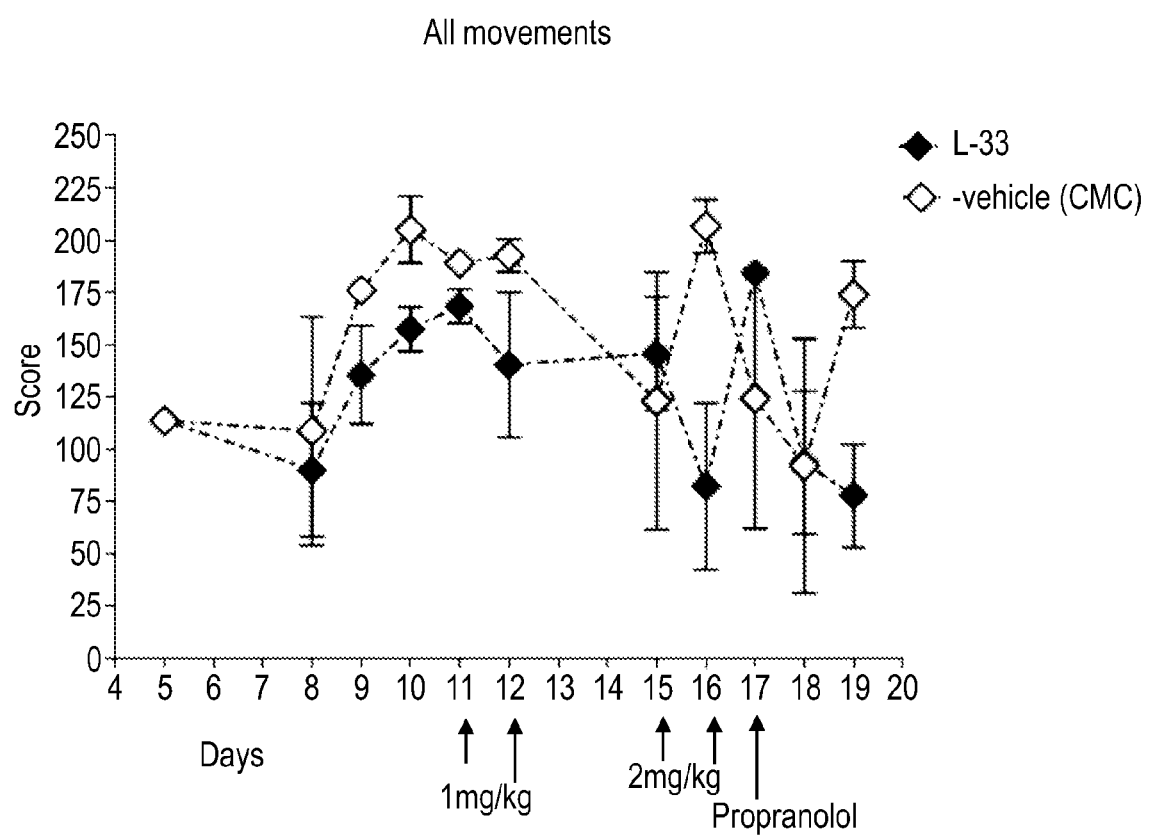

PIPERAZINE, PIPERIDINE AND TETRAHYDROPYRIDINE DERIVATIVES AND THEIR PHARMACEUTICAL USE

RELATED APPLICATIONS

This application is a division of U.S. patent application Ser. No. 13/322,572 filed on Nov. 28, 2011, which is a National Phase of PCT Patent Application No. PCT/IL2010/000418 having International filing date of May 26, 2010, which claims the benefit of priority of U.S. Provisional Patent Application No. 61/181,331 filed on May 27, 2009. The contents of the above applications are all incorporated by reference as if fully set forth herein in their entirety.

FIELD AND BACKGROUND OF THE INVENTION

The present invention, in some embodiments thereof, relates to a novel family of compounds and uses thereof to treat disorders such as central nervous system disorders, and more particularly, but not exclusively, novel compounds comprising a piperazine, piperidine or tetrahydropyridine moiety.

Piperazine derivatives which act on the central nervous system (CNS) are known in the art. For example, EP 512755 describes piperazine derivatives having high binding affinity to 5-HT receptors. Recently, piperazine derivatives (and also other nitrogen-containing six-membered rings, such as piperidine), which are substituted at positions 1 and 4 with a fused ring heterocyclic and phenyl groups, respectively, were described in WO 08/117,269. The compounds disclosed in WO 08/117,269 are reported to bind to dopamine and 5-HT receptors and to be useful in the treatment of various CNS disorders.

DESCRIPTION OF EMBODIMENTS OF THE INVENTION

The invention relates to a class of compounds of formula (I):

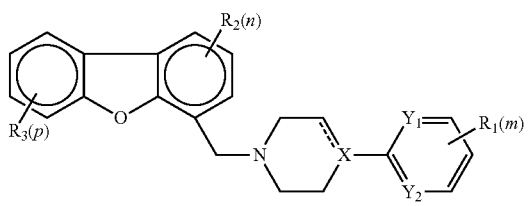

wherein:
$Y_1$ and $Y_2$ are independently CH, $C(R_1)$ or N;
X is N, CH or C, with the proviso that when X is C, then the broken line represents a chemical bond;
$R_1$, $R_2$ and $R_3$ are independently selected from the group consisting of C1-C5 alkyl, —OH, —SH, halogen, alkoxy, namely, —O(C1-C5alkyl), —$NR_42$, $NO_2$, —CN.
m is 0, 1, 2, 3, 4 or 5;
n is 0, 1, 2 or 3; and
p is 0, 1, 2, 3 or 4.

It is understood that when m, n, or p equals 0, then the free positions at the relevant ring are occupied by hydrogen atoms.

The compounds of formula I have been found to posses high binding affinity for dopamine and serotonin receptors. The compounds are accordingly useful in the treatment of various CNS disorders, as discussed in more detail below.

Preferably, X in formula I is nitrogen. More specifically, preferred sub-classes of compounds provided by the present invention are represented by formulas Ia, Ib, Ic, Id and Ie (in the formulas depicted below, the substituents on the dibenzofuran system have the meanings as set forth above):

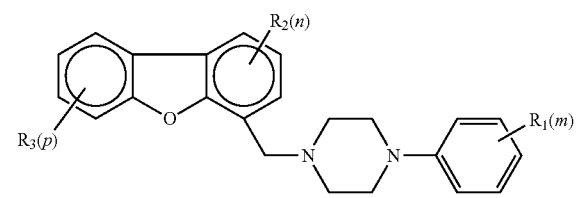
(Ia)

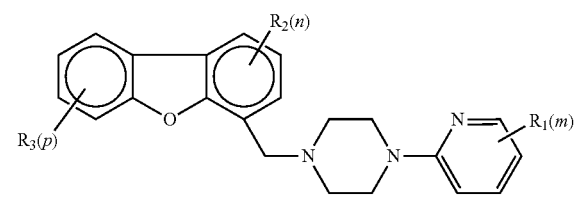
(Ib)

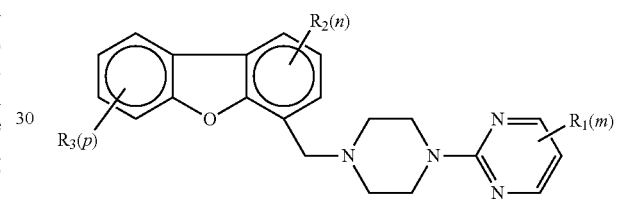
(Ic)

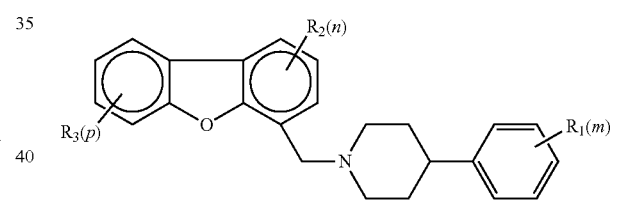
(Id)

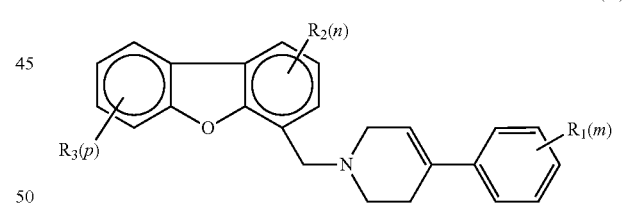
(Ie)

wherein m is 0, 1, 2 or 3, more preferably 0, 1 or 2, and when m is other than 0, then $R_1$ is preferably selected from the group consisting of hydroxy, alkoxy (specifically —OCH3 or —OC2H5), halogen and cyano.

The compounds of formula I may be prepared by reacting a piperazine, piperidine or 1,2,3,6-tetrahydropyridine derivative of formula II (or an acid addition salt thereof),

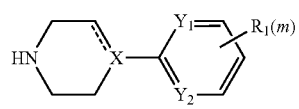
(II)

with dibenzofurane of formula III:

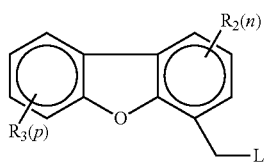
(III)

wherein X, Y1, Y2, R1, R2, R3 m, n and p are as hereinabove defined and L is a suitable leaving group such as halogen, (specifically chlorine or bromine), p-toluene sulfonate or mesylate). Thus, the reaction involves the formation of a tertiary amine by alkylation of a secondary amine (of formula II) with alkyl halide, tosylate or mesylate (of formula III). The reaction may be conveniently carried out in a solvent, which may be selected from the group consisting of dimethylformamide; ethers such tetrahydrofuran; acetonitrile, ketones such as acetone and methyl ethyl ketone; and halogenated hydrocarbons. The reaction is carried out in the presence of a base, which may be either an inorganic base (alkali or alkaline earth metal carbonate, alkali metal hydrogen carbonate and sodium hydroxide) or an organic base (trialkyl amine, such as triethylamine; or pyridine). dimethylformamide and triethylamine are generally the preferred solvent and base, respectively, employed in the reaction.

In practice, the solvent and the base are charged into a reaction vessel, following which the starting materials of formulas II and III are added and allowed to dissolve under stirring. The starting materials may be used in equimolar amounts, but it may be preferable to apply the starting material of formula II in a 1.5 molar excess. The reaction may be carried out under room temperature or possibly under heating. The reaction reaches completion after about 16 hours. The product of formula I may then be isolated from the reaction mixture by means of known procedures. More specifically, upon removal of the solvent by means of evaporation under reduced pressure, an the product of formula I may be recovered as an oily material which can be purified by means of silica gel column chromatography.

The reactants of formula II and III which participate in the synthetic pathway described above are commercially available, or may be prepared by conventional methods.

Regarding the starting material of formula III, a dibenzofurane system is most generally represented by the following formula:

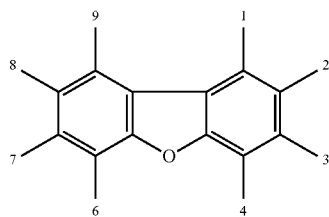

where the numbers 1-4 and 6-9 represent positions in which substituents may be provided. As indicated before, in the starting material of formula III, which is operative according to the present invention in the preparation of the end product of formula I, position 4 is occupied by the group —CH2L (wherein L is a leaving group). The starting material of formula III may be obtained by reducing a corresponding aldehyde, to form a dibenzofurane derivative having —CH2OH group attached at position 4, and subsequently converting said alcohol to the starting material of formula III, wherein the leaving group L is halogen, such as chlorine or bromine, as illustrated by the following sequential reaction scheme:

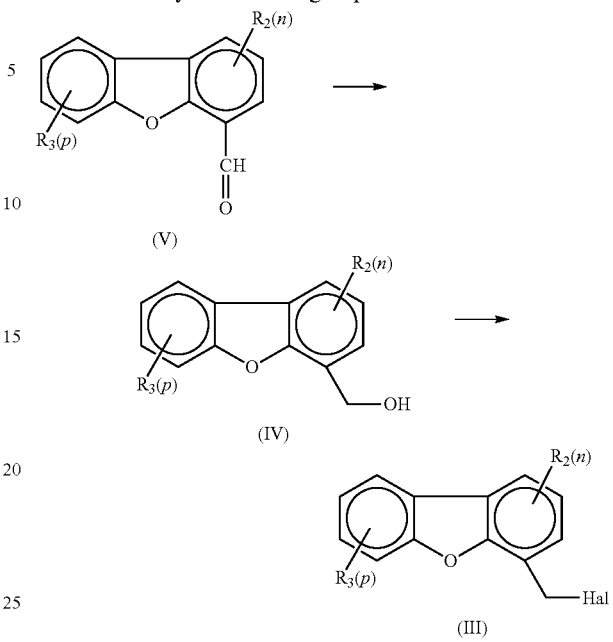

The reduction of the aldehyde of formula (V) to form the primary alcohol of formula (IV) may be conveniently accomplished in the presence of a hydride source, namely, a complex metal hydride, such as sodium borohydride or lithium aluminum hydride. A suitable solvent to employed in the reaction is typically a short chain alkanol, specifically methanol or ethanol. The primary alcohol intermediate is isolated from the reaction mixture and is subsequently treated with a halide source, such as thionyl chloride or various phosphorous halides. The conversion of the alcohol (IV) into the corresponding haloalkane (III).

The compounds the invention were tested for dopamine (D2, D3 and D4.4) receptors binding activity and $5\text{-HT}_{1A}$ receptor binding activity according to the procedures described in WO 08/117,269; the compounds of the invention were found to be potent ligands of said receptors. The compounds of the invention may be used in the treatment of CNS disorders in mammals, especially human. Of particular interest is the use of the compounds of the invention as anti-dyskinetic agents. Dyskinesia is a serious side effect associated with L-DOPA treatment of patients with Parkinson's disease. An in vivo study given below demonstrates that the compounds of the invention exhibit activity against L-DOPA induced dyskinesia in parkinsonian rats.

The invention also provides a pharmaceutical composition comprising the compound of formula (I) or a pharmaceutically acceptable salt thereof in combination with one or more pharmaceutically acceptable carriers. The composition may be provided either in a solid or liquid form, or a mixture of solid and liquid.

Suitable solid compositions include tablets, capsules, caplets, powders, granulates, sachets, lozenges and pastilles. Examples of excipients which are combined with the active ingredient to produce the composition include (but are not limited to) diluents or fillers (e.g. lactose, microcrystalline cellulose, pregelatinized starch), binders (e.g. carbopol, povidone, xanthan gum), lubricants (e.g. magnesium stearate), glidants (e.g. talc, colloidal silicon dioxide) and disintegrants (e.g. alginic acid, carboxymethylcellulose, carboxymethyl starch, croscarmellose sodium, sodium starch glycolate).

Solid unit dosage forms (e.g., tablets or capsules) may be manufactured by a variety of different methods, as are well known in the art, including a direct compression using a tablet punch. As an alternative to direct compression, the active ingredient and excipients may be combined by dry blending, and then subjected to dry granulation prior to tablet compression. A further alternative method is to utilize wet granulation, in which at least some of the excipients, together with the active ingredient, are blended and then further mixed in the presence of a granulation liquid. Following aggregation of the various powders, the aggregates (i.e. granules) are then sized by screening or milling, dried and used to produce a tablet. The tablet may be finally coated.

Solid formulation blends for loading into capsules (such as soft gelatin capsules) may be prepared by dry blending, or by wet or dry granulation prior to being introduced into said capsules.

Suitable liquid compositions include, inter alia, solutions, suspensions and syrups, in which solvents (e.g. water, an organic solvent) emulsifying agents (e.g. carbomer, cetyl alcohol, gelatin), flavoring agents (e.g. vanillin, fruit acids, menthol), sweeteners (e.g. sucrose, fructose, aspartame, saccharin) and preservatives may be present together with the active compound of formula I.

In addition to orally-administrable compositions, the compounds of the invention may be formulated into sterile solution for intravenous or intramuscular injection.

Further information relating to the preparation of solid, liquid and gel dosage forms that are suitable for use in the present invention may be obtained from any standard pharmaceutical reference work, such as Remington's Pharmaceutical Science (Martin E W [1995], Mack Publishing Company, 19th ed.).

A further aspect of the invention relates to the use of a compound of formula I set forth herein above in the preparation of a medicament, e.g., for the treatment of CNS disorders in a mammal, and more specifically, for the treatment of dyskinesia.

The present invention also relates to a method for treating CNS disorders in a patient, comprising administering a therapeutically effective amount of a compound of formula I. It is to be understood that the dosages may vary depending upon the requirements of the patient, the severity of the disorder being treated, and the particular compound being used. If desired, the daily dose may also be divided into multiple doses for administration, e.g., two to four times per day. The compounds of Formula I according to this invention may be administered orally or parenterally.

BRIEF DESCRIPTION OF THE DRAWINGS

FIG. 1 is a graph illustrating the results of an in vivo activity study in which a compound of the invention was tested as an anti-diskinesia agent.

EXAMPLES

Preparation 1

Preparation of 4-(chloromethyl) Dibenzofuran (A starting material of Formula III)

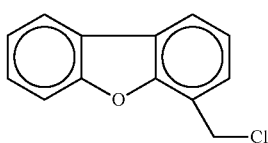

a) Dibenzofuran-4-ylmethanol 1 g (5.1 mmol) of Dibenzofuran-4-carboxaldehyde is dissolved in 5 ml of ethanol. 0.24 g of $NaBH_4$ is then added portionwise to the stirred solution during a period 20 minutes. The solution is maintained under stirring at room temperature for 2 hours, following which the solvent is evaporated. The residue obtained is treated with water, and aqueous layer is then extracted with ether. Evaporation of the organic phase yielded 0.90 g of Dibenzofuran-4-ylmethanol.

b) 4-(chloromethyl) Dibenzofuran

Thionyl chloride (6 ml) is added to a solution of Dibenzofuran-4-ylmethanol (0.9 g). The solution is refluxed for 1 hour. Excess of reagent is evaporated to yield 4-(chloromethyl) Dibenzofuran (0.97 g).

Example 1 (L32)

4-(chloromethyl) Dibenzofuran (0.34 g, 1.7 mmol) and 1-(2-ethoxyphenyl)piperazine hydrochloride (0.62 g, 2.55 mmol) are added to a stirred solution of N,N Dimethylformamide (5 ml) and triethylamine (1 ml). The solution formed is stirred at room temperature for 24 hours. The solvent is then evaporated under reduced pressure and the crude residue obtained was chromatographed on silica gel with eluant hexane:ethyl acetate (90% Hexane/10% Ethyl Acetate). Following recrystallization from hexane, the product was collected in a solid form (120 mg).

$H^1$NMR: 1.10 (t, 3H), 2.82 (t, 2H), 3.27 (t, 2H), 4.02 (s, 2H), 4.21 (q, 2H) 7.10-8.05 (m, 10H, arom).

Example 2 (L33)

4-(chloromethyl) Dibenzofuran (0.34 g, 1.7 mmol) and 1-(3-hydroxyphenyl) piperazine (0.50 gr. (2.55 mmol) are added to a stirred solution of N,N Dimethylformamide (5 ml) and triethylamine (1 ml). The solution formed is stirred at room temperature for 24 hours. The solvent is then evaporated under reduced pressure and the crude residue obtained is chromatographed on silica gel with eluant hexane:ethyl acetate (80% Hexane/20% Ethyl Acetate). Following recrystallization from hexane, the product is collected in a solid form (390 mg).

$H^1$NMR: 2.84 (t, 2H), 3.31 (t, 2H), 4.07 (s, 2H), 6.92-7.91 (m, 11H, arom).

Example 3 (L34)

4-(chloromethyl) Dibenzofuran (0.34 g, 1.7 mmol) and 4-phenyl-1,2,3,6-tetrahydropyridine hydrochloride (0.50 g) are added to a stirred solution of N,N Dimethylformamide (5 ml) and triethylamine (1 ml). The solution formed is stirred at room temperature for 24 hours. The solvent is then evaporated under reduced pressure and the crude residue obtained is chromatographed on silica gel with eluant hexane:ethyl acetate (90% Hexane/10% Ethyl Acetate). Following recrystallization from hexane, the product is collected in a solid form (100 mg).

$H^1$NMR: 2.78-3.95 (m, 6H), 4.03 (s, 2H), 4.55 (m, 1H) (6.93-8.82 (m, 12H, arom)

Example 4 (L105)

4-(chloromethyl) Dibenzofuran (1 g, 5 mmol) and 4-phenyl piperidine (1.2 g, 7.55 mmol) are added to a stirred solution of N,N Dimethylformamide (10 ml) and triethylamine (2 ml). The solution formed is stirred at room temperature for 24 hours. The solvent is then evaporated under reduced pressure and the crude residue obtained is chromatographed on silica gel with eluant hexane:ethyl acetate (90% Hexane/10% Ethyl Acetate) to give the product (195 mg)

H¹NMR: 2.18-3.88 (m, 9H, piperidine), 4.03 (s, 2H), (6.90-8.72 (m, 12H, arom)

Example 5 (L106)

4-(chloromethyl) Dibenzofuran (0.78 g, 4 mmol) and 2-thiazole piperazine (1 g, 6 mmol) are added to a stirred solution of N,N Dimethylformamide (10 ml) and triethylamine (2 ml). The solution formed is stirred at room temperature for 24 hours. The solvent is then evaporated under reduced pressure to give a crude residue, which is chromatographed on silica gel with eluant hexane:ethyl acetate (90% Hexane/10% Ethyl Acetate) to afford the product (204 mg).
H¹NMR: 2.86 (t, 2H), 3.28 (t, 2H), 4.03 (s, 2H), (6.92-8.89 (m, 9H, arom)

Example 6 (L107)

4-(chloromethyl) Dibenzofuran (0.78 g, 4 mmol) and 1-(-2-methoxyphenyl) piperazine hydrochloride (1.4 g, 6 mmol) are added to a stirred solution of N,N Dimethylformamide (10 ml) and triethylamine (2 ml). The solution formed is stirred at room temperature for 24 hours. The solvent is then evaporated under reduced pressure to give a crude residue, which is chromatographed on silica gel with eluant hexane:ethyl acetate (90% Hexane/10% Ethyl Acetate) to afford the product (411 mg).
H¹NMR: 2.81 (t, 2H), 3.21 (t, 2H), 4.02 (s, 2H), 4.21 (s, 3H) 7.09-8.09 (m, 10H, arom).

Example 7 (L108)

4-(chloromethyl) Dibenzofuran (0.78 g, 4 mmol) and 1-(-2-pyridyl) piperazine (0.8 g, 5 mmol) are added to a stirred solution of N,N Dimethylformamide (10 ml) and triethylamine (2 ml). The solution formed is stirred at room temperature for 24 hours. The solvent is then evaporated under reduced pressure to give a crude residue, which is chromatographed on silica gel with eluant hexane:ethyl acetate (80% Hexane/20% Ethyl Acetate) to afford the product (223 mg).
H¹NMR: 2.87 (t, 2H), 3.25 (t, 2H), 4.1 (s, 2H), 7.09-8.17 (m, 10H, arom).

Example 8 (L109)

4-(chloromethyl) Dibenzofuran (0.78 g, 4 mmol) and 1-(-2-cyanophenyl) piperazine (0.9 g, 5 mmol) are added to a stirred solution of N,N-Dimethylformamide (10 ml) and triethylamine (2 ml). The solution formed is stirred at room temperature for 24 hours. The solvent is then evaporated under reduced pressure to give a crude residue, which is chromatographed on silica gel with eluant hexane:ethyl acetate (90% Hexane/20% Ethyl Acetate) to afford the desirable product (180 mg)
H¹NMR: 2.86 (t, 2H), 3.28 (t, 2H), 4.05 (s, 2H), 6.96-7.97 (m, 11H, arom).

Example 9 (L110)

4-(chloromethyl) Dibenzofuran (0.78 g, 4 mmol) and 1-(-2-pyrimidyl) piperazine (1 g, 6 mmol) are added to a stirred solution of N,N Dimethylformamide (10 ml) and triethylamine (2 ml). The solution formed is stirred at room temperature for 24 hours. The solvent is then evaporated under reduced pressure to give a crude residue, which is chromatographed on silica gel with eluant hexane:ethyl acetate (80% Hexane/20% Ethyl Acetate) to afford the product (503 mg)
H¹NMR: 2.84 (t, 2H), 3.27 (t, 2H), 4.1 (s, 2H), 7.04-8.27 (m, 9H, arom).

Example 10

The compounds of Examples 1, 3, 4 and 9 were tested for their $5-HT_{1A}$ receptor binding activity and dopamine (D2, D3 and D4.4) receptors binding activity according to the protocols set forth above. The percentage inhibition of labeled ligand binding caused by the indicated few test ligand compound of the invention at different concentrations of said test ligand is shown in Table I.

TABLE I

| Compound, 1micrMol | $5-HT_{1A}$ binding | D2 binding | D3 binding | D4 binding |
|---|---|---|---|---|
| L-33 | 43.4 | 75% | 78.2 | 77.7 |
| L-109 | 73.5 | 68.7 | 63.2 | 64.9 |
| L-107 | 86.7 | 96% | 33.7 | 78 |
| L-105 | 42.2 | 93.8 | 44.5 | 69.1 |

The results demonstrate that the compounds of the invention strongly bind to both D2, D3 and D4 dopamine and $5-HT_{1A}$ receptors.

Example 11

In the following study, the compound of Example 2 was tested for its in vivo activity against L-DOpA induced dyskinesia in parkinsonian rats (the model is the L-DOPA-induced abnormal involuntary movements (AIMS) in the 6-hydroxydopamine (6-OHDA) lesion rat model).

Rats were unilaterally lesioned with (6-OHDA) in medial forebrain bundle. Three weeks later, rats were injected with apomorphine (0.1 mg/kg s.c.) and numbers of contralateral turns were counted using a rotameter. Two weeks after the apomorphine test, rats showing marked turning activity were selected and split into 2 groups:

The experimental group, which received the compound of Example 2, and the control group, which received the injection medium for said compound (CMC in saline); n=5 and 3 respectively.

All animals were treated daily with L-dopa/carbidopa (25/6 mg/kg respectively) and dyskinetic movements were scored commencing day 5. Compounds were administered in escalating dose, at daily doses shown below, commencing day 11 of L-dopa treatment: 1 mg/kg—11$^{th}$ day, 1 mg/kg—12$^{th}$, 2 mg/kg—15$^{th}$, 2 mg/kg—16$^{th}$. On the 17$^{th}$ day, the rats of the control group were injected with propranolol (10 mg/kg in saline), whereas the rats of the experimental group were injected with saline. On the 18$^{th}$ and 19$^{th}$ day all rats were treated with L-dopa/carbidopa only.

The following dyskinetic movements were scored: dystonic posturing, head and upper body movements, forelimb, locomotion, trunk, orolingual. Movements were scored according to the protocol shown in Table II.

TABLE II

| SCORE | DYSTONIC POSTURING | HEAD AND UPPER BODY MOVEMENTS | LIMB MOVEMENTS | LOCOMOTIVE MOVEMENTS | OROLINGUAL & OROFACIAL MOVEMENTS |
|---|---|---|---|---|---|
| 0-4 | head and body turning towards the side | head movements and | abnormal, purposeless movements | locomotion movements contralaterally to | empty jaw movements, contralateral |

TABLE II-continued

| SCORE | DYSTONIC POSTURING | HEAD AND UPPER BODY MOVEMENTS | LIMB MOVEMENTS | LOCOMOTIVE MOVEMENTS | OROLINGUAL & OROFACIAL MOVEMENTS |
|---|---|---|---|---|---|
| | contralateral to the lesion | choreiform twisting of the neck and upper body | of the forelimb and digits contralateral to the lesion | the lesion | tongue protrusion tremor of face muscles, gritting of the teeth |
| 0 0.5 very weak or single movements | absent of light or single turning of the head towards the side contralateral to the lesion with angle of bias about 30° | movements very weak or single head movements | absent of weak forelimb swings | movements ~1 rotation in 1 minute | single opening of the mouth, single tongue protrusion, tremor of face muscles, gritting of teeth |
| 1 weak movements | turning of the head at the point of the forelimb (angle of bias about 90°) | frequent little head movements | forelimb movements along the ground of the case or distinct, but rare movements with lifted forelimb | ~2-5 rotations in 1 minute | hardly seen, but permanent jaw movements with close mouth, rare tongue protrusion |
| 2 moderate movements | turning of the head at the point of the back paw (angle of bias about 150°) | moderate and distinctly seen head movements and choreiform twisting of the neck | steady moderate movements with lifted forelimb | ~6-10 rotations in 1 minute | permanent jaw movements with a little opening mouth, more often tongue protrusion |
| 3 strong movements | turning of the head at the point of the tail (angle of bias about 180°) | strong head movements and choreiform twisting of the neck and upper body | fast plentiful movements with lifted forelimb | ~11-18 rotations in 1 minute | permanent jaw movements with a broadly opening mouth, frequent tongue protrusion |
| 4 very strong movements | turning of the head over the tail with the angle bias more than 180° | strong head movements, choreiform twisting of the neck and upper body, throwing back the head | rapid movements of lifted forelimb with large scale | more than 18 rotations in a minute | |

The results are presented in FIG. 1, AIM score is shown for the relevant treatment days (for the sum of all movements indicated in Table II together). A strong anti-dyskinetic effect is observed on the 16$^{th}$ day, in which day the compound of the invention was administered (for the second time in succession) at a daily dose of 2 mg/kg. It is noted that Propanolol, which was given to the control group in a dose of 10 mg/kg on the 17$^{th}$ day, reduced the abnormal involuntary movements.

What is claimed is:

1. A compound of the general formula Id or the general formula Ie:

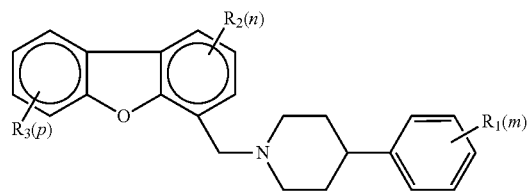

(Id)

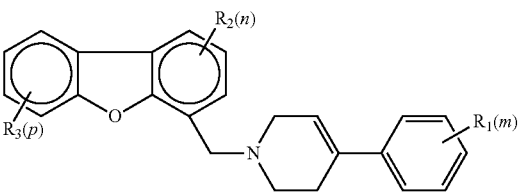

(Ie)

wherein:

$R_1$, $R_2$ and $R_3$ are independently selected from the group consisting of C1-C5 alkyl, —OH, —SH, halogen, alkoxy, $NO_2$, and —CN;

m is 0, 1, 2, 3, 4 or 5;

n is 0, 1, 2 or 3; and p is 0, 1, 2, 3 or 4.

2. A compound according to claim 1, wherein m is 0, 1, 2 or 3, and $R_1$ is selected from the group consisting of hydroxy, alkoxy, halogen and cyano.

3. A compound according to claim 1, wherein $R_1$ is hydroxy.

4. A compound according to claim 1, wherein m is 1.

5. A compound according to claim 1, wherein n is 0 and p is 0.

6. A pharmaceutical composition comprising a compound as defined in claim 1 in combination with one or more pharmaceutically acceptable carriers.

7. A method for treating CNS dyskinesia in mammals, comprising administering to said mammal a therapeutically effective amount of the compound defined in claim 1.

8. A compound of formula I:

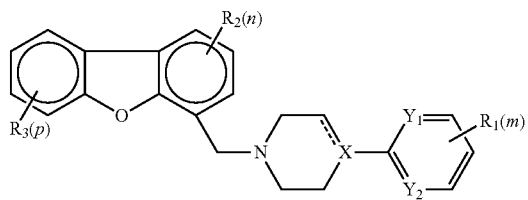

wherein:
$Y_1$ and $Y_2$ are independently CH, C($R_1$) or N;
X is CH or C, with the proviso that when X is C, then the broken line represents a chemical bond;
$R_1$, $R_2$ and $R_3$ are independently selected from the group consisting of C1-C5 alkyl, —OH, —SH, halogen, alkoxy, $NO_2$, and —CN;
m is 0, 1, 2, 3, 4 or 5;
n is 0, 1, 2 or 3; and
p is 0, 1, 2, 3 or 4.

9. A compound according to claim 8, having the formulas Id or Ie:

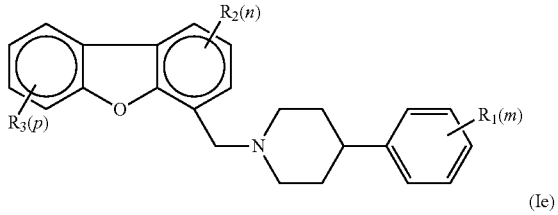

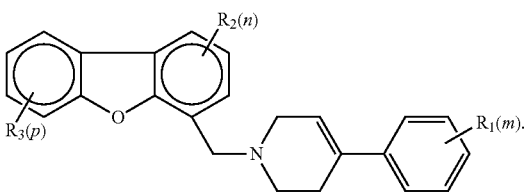

10. A compound according to claim 8, wherein m is 0, 1, 2 or 3, and $R_1$ is selected from the group consisting of hydroxy, alkoxy, halogen and cyano.

11. A compound according to claim 8, wherein $R_1$ is hydroxy.

12. A compound according to claim 8, wherein m is 1.

13. A compound according to claim 8, wherein n is 0 and p is 0.

14. A pharmaceutical composition comprising a compound as defined in claim 8 in combination with one or more pharmaceutically acceptable carriers.

15. A method for treating CNS dyskinesia in mammals, comprising administering to said mammal a therapeutically effective amount of the compound defined in claim 8.

* * * * *